United States Patent [19]

Sullivan

[11] Patent Number: 4,928,669
[45] Date of Patent: May 29, 1990

[54] STRAIGHTENING DEVICE FOR FLEXIBLE TUBULAR STRUCTURES

[76] Inventor: Michael J. Sullivan, 1116 Radcliffe Ave., Kingsport, Tenn. 37664-2026

[21] Appl. No.: 371,311

[22] Filed: Jun. 26, 1989

[51] Int. Cl.$^5$ ............................................. A61B 1/00
[52] U.S. Cl. ........................................ 128/4; 128/772
[58] Field of Search ............... 128/3, 4, 5, 6, 7, 8, 128/772

[56] References Cited

U.S. PATENT DOCUMENTS

| | | | |
|---|---|---|---|
| 3,547,103 | 12/1970 | Cook | 128/772 |
| 3,847,140 | 11/1974 | Ayella | 128/772 |
| 3,854,473 | 12/1974 | Matsuo | 128/8 |
| 4,043,323 | 8/1977 | Komiya | 128/4 |
| 4,215,703 | 8/1980 | Willson | 128/772 |
| 4,732,163 | 3/1988 | Bonello et al. | 128/772 |

Primary Examiner—William H. Grieb

[57] ABSTRACT

A straightening device for endoscopic instruments or the like, the device having an elongated cable provided with a shoulder adjacent its distal end, an elongated, normally flexible non-compressible, coiled wire sheath surrounding the cable in sliding contact therewith, the coils of the sheath normally contacting each other, the distal end of the sheath being in abutment with the distal shoulder of the cable, a bearing block having a bore non-rotatably, slidably receiving a proximal end portion of the cable, stop on the bearing block in abutment with the proximal end of the sheath, and a power generating element adapted to forcibly engage the bearing block and the proximal end portion of the cable to place the cable in tension and apply straightening force to the sheath.

6 Claims, 1 Drawing Sheet

STRAIGHTENING DEVICE FOR FLEXIBLE TUBULAR STRUCTURES

BACKGROUND OF THE INVENTION

This invention concerns a device for applying straightening force to flexible tubular structures, particularly extended medical instruments such as fiberscopes, fiber optic colonoscopes and remote controlled biopsy tools, whereby the instrument, particularly the highly flexible leading end thereof, can be selectively straightened in a very accurate manner and to various degrees for straightening surrounding twisted or tortuous body passages or conduit for advancing the instrument therethrough.

Such medical instruments are described in the Olympus Optical Co., Ltd. (Olympus Tokyo) instructional manual entitled "Olympus CF type 10L/I/M" incorporated herein by reference.

In general, these endoscopic instruments must be quite flexible, even floppy, especially at the distal end, in order to follow rather than prod the sensitive and rupturable tissue of the stomach, esophagus, intestines or the like. Often, however, a deep insertion such as is common in colonoscopy will encounter twisted or severely bent body conduit which must be brought to a straighter condition to allow advancement of the instrument therethrough.

Stiffening devices have been proposed for insertion into an accessory channel or tubular passage in such endoscopic instruments in order to reduce the flexibility thereof. Such devices are shown in U.S. Pat. Nos. 3,854,473 and 4,215,703, the disclosures of which are incorporated herein by reference, and employ an elongated coiled wire compression spring or closely wound helix, axially positioned in the endoscope, wherein the spring rigidity and hence the endoscope stiffness is controlled by adjusting the spacing between the spring coils helical windings. Such a compression of the 3,854,473, however, does not afford the real straightening force necessary for actually straightening the endoscope, particularly its floopy distal leading end, and the adjacent and more difficult body conduit portions, while also providing, upon demand, the necessary flexibility for following normal contours, without excessive prodding or thrusting particularly where easily rupturable tissue is involved. Likewise, the handle structure of the 4,215,703 patent necessarily imparts very undesirable rotation to the inner core and outer coil when applying tension to the core. Such rotation can defeat the purpose of the stiffener, the degree of tension, i.e. the heavy tension considered necessary by applicant is not readily achievable by the handle structure of this patent.

A principal object of the present invention therefore is to provide a means for applying accurate straightening force to endoscopic or other such intruments over an extremely wide range of straightening force in order to accommodate practically all insertion situations encountered in the use of such instruments.

SUMMARY OF THE INVENTION

The above and other objects hereinafter becoming evident have been attained in accordance with the present invention which is defined in its broad sense as a straightening device for endoscopic instruments or the like and adjacent body passages or conduit, comprising an elongated cable having shoulder means adjacent to its distal end, an elongated, normally flexible noncompressible, coiled wire sheath surrounding said cable in sliding contact therewith, the adjacent coils of said sheath always contacting each other over at least a portion of their adjacent surface, the distal end of said sheath being in abutment with said distal shoulder means of said cable, bearing block means having bore means slidably receiving a proximal end portion of said cable, slide bar means axially, non-rotatably slidably mounted in said bore means, said proximal end portion of said cable being affixed to said slide bar means, stop means on said block means in abutment with the proximal end of said sheath, a threaded shaft segment affixed to said slide bar means and slidably extending through a distal portion of said bore means and nut means threadedly mounted on said segment and adapted to abut said block means when rotated relative to said segment to tension said cable and apply straightening force to said sheath.

In certain preferred embodiments:
(a) the cable is a wire;
(b) the cable is removable affixed to said slide bar means;
(c) the nut means has at least one diameter of more than 1.5 inches;
(d) the ratio of the diameter of the nut means to the threaded shaft segment is at least about 4.0; and
(e) the slide means, block means, sheath and cable are all readily disassemblable for cleaning or repair.

BRIEF DESCRIPTION OF THE DRAWINGS

The invention will be further understood from the following description and drawings wherein.

DETAILED DESCRIPTION OF PREFERRED EMBODIMENTS OF THE INVENTION

Figure 1:
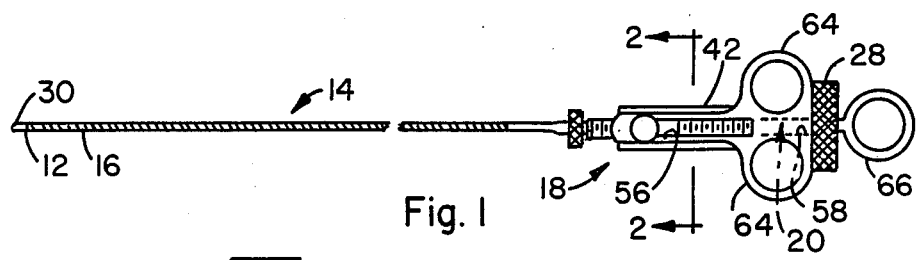
FIG. 1 is a top elevational view of the present straightening device.
Figure 2:
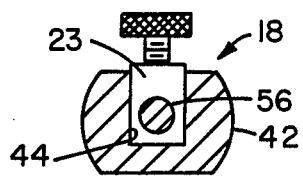
FIG. 2 is a cross-sectional view, shown enlarged to approximate actual size, taken along line 2—2 of FIG. 1 in the direction of the arrows.
Figure 3:
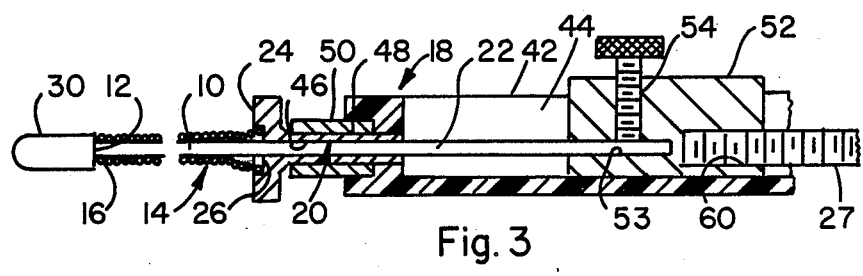
FIG. 3 is an enlarged vertical sectional view of the sheath and adjacent portions of the stop means and bearing block means of the device of FIG. 1.
Figure 4:
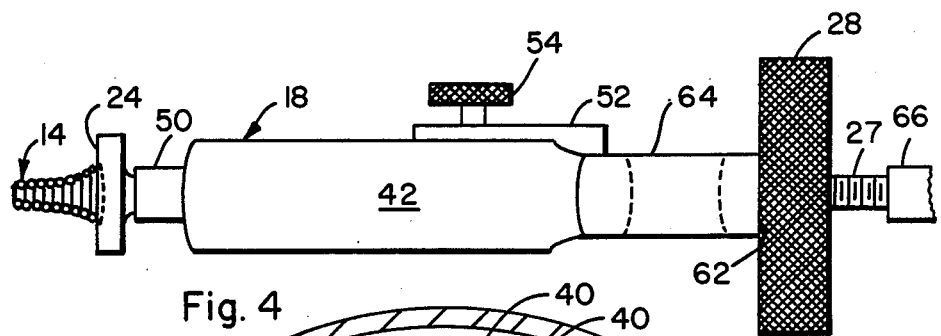
FIG. 4 is a side elevational view of the device of FIG. 1.

Referring to the drawings, and with reference to claim 1 hereof, the present straightening device comprises an elongated, normally highly flexible cable 10 having shoulder means 12 adjacent its distal end, an elongated, normally flexible, non-compressible, coiled wire sheath 14 surrounding said cable in sliding contact therewith, the coils of said sheath normally contacting each other, the distal end 16 of said sheath being in abutment with said distal shoulder means 12 of said cable, bearing block means 18 having bore means generally designated 20 slidably receiving a proximal end portion generally designated 22 of said cable, slide bar means 23 axially, non-rotatably slidably mounted in said bore means, stop means 24 on said bearing block means in abutment with the proximal end 26 of said sheath, a threaded shaft segment 27 affixed to said slide bar means and slidably extending through a distal portion of said bore means, and nut means 28 threadedly mounted on said segment and adapted to abut said block means when rotated relative to said segment to tension said cable and apply straightening force to sheath.

More specifically, the cable 10 can be of any strong, tensionable material including polymeric such as Nylon, polyimide or polyolefin, or metal such as brass, copper or preferably stainless steel, and can be a single wire or braided or twisted multi-filament cable. The requirements, however, are that it be strong under tension, preferably non-stretchable, and normally highly flexible. The shoulder means 12 is provided by rearward surface of a head 30 firmly secured to or formed integrally with the cable 10.

Figure 5:
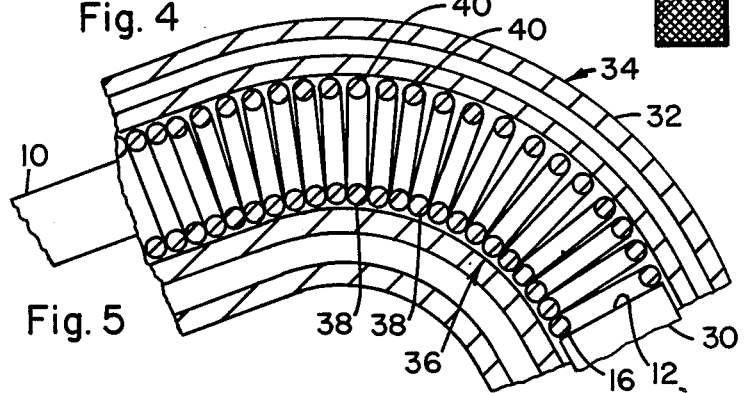
FIG. 5 is a greatly enlarged, partially sectioned, longitudinal view of the distal end portion of the device and surrounding portions of an endoscope.

The sheath 14 construction, preferably of stainless steel, is highly critical in that its properties must be such that it can be brought very rapidly from an essentially neutral and flexible condition to a condition wherein it exerts a considerable straightening force at least to the proximal, floppy distal end 32 of the endoscopic or other such instrument 34 shown in FIG. 5. The only way this can be achieved is through the essentially non-compressibility of the wire coils in their angularly disposed condition, by means of their intrinsic contact with each other on the concave side 36 of the bend. The points of contact 38 of the coils or turns serve as fulcrums for levering the convex sides 40 of the coils together such as to exert a large straightening force to the surrounding floppy, distal end of the endoscopic instrument and surrounding body conduit.

The bearing block 18 may be widely varied in both materials of construction and shape. It is preferred that the body portion 42 thereof be of a strong plastic material such as mentioned above, but, of course, it can also be metal. This block is formed with a slot 44 communicating at each end with the bore 20. The forward portion 46 of the bore is provided, in the exemplary embodiment of the drawing, by metal sleeve 48 provided on its forward end with the stop 24. A metal bushing 50 permanently affixed into the forward end of the block frictionally but removably receives sleeve 48. A connector slide bar 52 is slidably mounted in slot 44 and receives end 22 of the cable in a socket 53. A set screw 54 is threaded into the bar and locks the cable end into socket 53. A threaded shaft 56 is slidable within the rearward portion 58 of bore 20 and is non-rotatably locked into threaded socket 60 in bar 52, e.g., by forcible bottoming out or cementing or the like therein. The power means 28 in the form of a nut is threadedly mounted on shaft 56 and is adapted to be rotated thereon against the rearward surface 62 of block 42 to putt cable 10 to the right in FIG. 1 to tension the same and straighten the sheath. Reverse rotation of nut 28 will remove the tension. The slide bar 52 will, of course, prevent rotation of the cable during the tensioning operation and prevent misdirection of the straightening force. Convenient apertured handle segments 64 on the block and 66 on the shaft are provided for ease of operation and gripping of the device.

With reference to the broad claim language and drawing hereof, the bore means 20 comprises the forward bore section 46, the intermediate section or slot 44 and the rearward bore section 58, and the proximal end portion of said cable comprises the section 22 which slides through sleeve 48, the connector slide bar 52, and the threaded shaft 56 which slides through rearward bore section 58.

The invention has been described in detail with particular reference to preferred embodiments thereof, but it will be understood that variations and modifications will be effected within the spirit and scope of the invention.

I claim:

1. A straightening device for tubular medical instruments or the like, comprising an elongated cable having shoulder means adjacent its distal end, an elongated, normally flexible, non-compressible, coiled wire sheath surrounding said cable in sliding contact therewith, the adjacent coils of said sheath always contacting each other over at least a portion of their adjacent surfaces, the distance end of said sheath being in abutment with said distal shoulder means of said cable, bearing block means having bore means slidably receiving a proximal end portion of said cable, slide bar means axially, non-rotatably slidably mounted in said bore means, said proximal end portion of said cable being affixed to said slide bar means, stop means on said block means in abutment with the proximal end of said sheath, a threaded shaft segment affixed to said slide bar means and slidably extending through a distal portion of said bore means, and nut means threadedly mounted on said segment and adapted to abut said block means when rotated relative to said segment to tension said cable and apply straightening force to said sheath.

2. The device of claim 1 wherein said cable is a wire.

3. The device of claim 1 wherein said cable is removably affixed to said slide bar means.

4. The device of claim 1 wherein the ratio of the diameters of said nut means to said threaded shaft segment is at least about 4.0.

5. The device of claim 1 wherein said slide means, block means, sheath and cable are all readily disassemblable for cleaning or repair.

6. An endoscopic instrument having at least a substantial portion of the cable and sheath of the device of claim 1 slidably mounted in an elongated passageway therein and extending axially thereof.

* * * * *

UNITED STATES PATENT AND TRADEMARK OFFICE
CERTIFICATE OF CORRECTION

PATENT NO. : 4,928,669

DATED : 05/29/90

INVENTOR(S) : Michael J. Sullivan

It is certified that error appears in the above-identified patent and that said Letters Patent is hereby corrected as shown below:

Claim 1, line 8, in that "distance" should be "distal".

Signed and Sealed this

Seventeenth Day of March, 1992

Attest:

HARRY F. MANBECK, JR.

Attesting Officer

Commissioner of Patents and Trademarks